United States Patent [19]

Fain

[11] Patent Number: 5,709,711
[45] Date of Patent: Jan. 20, 1998

[54] IMPLANTABLE DEFIBRILLATOR WITH ELECTROPHYSIOLOGIC TESTING CAPABILITIES

[75] Inventor: Eric S. Fain, Menlo Park, Calif.

[73] Assignee: Pacesetter, Inc., Sunnyvale, Calif.

[21] Appl. No.: 689,631

[22] Filed: Aug. 13, 1996

[51] Int. Cl.$^6$ .................................................. A61N 1/00
[52] U.S. Cl. ............................................................. 607/8
[58] Field of Search ................................ 607/5, 6, 7, 8, 607/30, 31, 32

[56] References Cited

U.S. PATENT DOCUMENTS

| | | |
|---|---|---|
| 4,316,472 | 2/1982 | Mirowski et al. . |
| 4,515,160 | 5/1985 | Keimel . |
| 5,279,293 | 1/1994 | Andersen et al. ............................ 607/5 |
| 5,350,403 | 9/1994 | Stroetmann et al. ......................... 607/5 |
| 5,397,336 | 3/1995 | Hirschberg et al. .......................... 607/5 |

OTHER PUBLICATIONS

HVS®-02 Cardiac Electrophysiology Device Operator's Manual, Ventritex, Inc. Jan. 1993.
7218 Arrhythmia Management Device Programming Guide, Medtronic, Inc., May 1994, pp. 7-1-7-45.
Ventak®MINI™ Physician's System Manual, CPI, pp. 74-83.

*Primary Examiner*—Scott M. Getzow
*Attorney, Agent, or Firm*—Steven M. Mitchell

[57] ABSTRACT

A method and apparatus for performing electrophysiologic testing on a patient's heart using an implantable pulse generator system. The system includes an implantable pulse generator such as an implantable cardioverter-defibrillator having high voltage capacitors for storing electrical energy to defibrillate the patient's heart, a means for inducing a cardiac arrhythmia, an electrode system for discharging the stored energy into the patient's heart, and an external programmer for communication with and command of the implantable pulse generator. The method comprises the steps of charging the capacitors to a selected energy level upon command from the external programmer, inducing fibrillation in the patient's heart following the charging step, and discharging the capacitors through the electrodes into the patient's heart to defibrillate the patient's heart. The method and system provides flexibility in electrophysiologic testing by allowing the physician to control the time of delivery of high voltage therapy.

15 Claims, 2 Drawing Sheets

5,709,711

IMPLANTABLE DEFIBRILLATOR WITH ELECTROPHYSIOLOGIC TESTING CAPABILITIES

BACKGROUND OF THE INVENTION

1. Field of the Invention

The present invention relates generally to implantable defibrillators and more particularly to an implantable defibrillator which can be used to perform electrophysiologic testing on a patient.

2. Prior Art

Implantable cardioverter defibrillators (ICDs) are implantable medical devices which are implanted in a patient, typically in the pectoral region, for the detection and treatment of tachyarrhythmias. The ICD is coupled to the patient's heart through transvenous leads which are used to sense electrical signals from the heart and to deliver both low voltage and high voltage electrical therapy to the heart. The most serious form of tachyarrhythmia is ventricular fibrillation which is usually fatal if not treated within a few minutes of occurrence.

In connection with the implant procedure for an ICD and also sometimes at follow-up clinical visits it is necessary to induce a tachyarrhythmia in the patient's heart to determine if the ICD is functioning properly and if its parameters have been optimally programmed. This may include induction of fibrillation and delivery of shocks to determine the defibrillation threshold (DFT) for the particular patient. This allows the physician to program the defibrillation shocks with an appropriate safety margin. It also allows the physician at the time of implant to determine if the ICD can be implanted with the selected electrode configuration since the ICD may not have enough energy output to provide a safety margin (typically about 10 joules) over the determined DFT. It may also allow, for example, programming parameters for the most effective antitachycardia pacing (ATP) detection and therapy algorithms for identification and termination of ventricular tachycardias. Further, the DFT testing may be used to allow the physician to select among several models of ICDs with different energy output. Typically the lower output device will have shorter charge times for its high voltage capacitors and/or be smaller in size.

One device which is currently used in implant procedures is the HVS®-02 high voltage stimulator available from Ventritex, Inc. This diagnostic device is an external device which can deliver to the patient through electrical leads connected to the heart programmable pacing pulses, cardioversion shocks and high voltage defibrillation shocks substantially similar to those from an ICD. This device is also capable of delivering programmed stimulation to the patient to assist the physician in electrophysiologic evaluation of the patient. Critically timed pulses can be used for inducing fibrillation in the heart. It would be desirable if the functions of this device could be incorporated directly into the ICD to eliminate the need for the high voltage stimulator.

In U.S. Pat. No. 4,316,472 to Mirowski et al, a command atrial cardioverter is disclosed. The system allows either a patient or a physician to command an implanted cardioverter to deliver a cardioversion pulse in response to an atrial arrhythmia. The delivered pulse may be synchronized to a sensed QRS complex. In one disclosed embodiment, the physician can select with an external programmer the level of cardioverting energy to be delivered by the cardioverter. The patent does not discuss use of the system in electrophysiologic testing.

It is known to provide some functions for assistance in electrophysiologic testing in implanted devices. U.S. Pat. No. 5,129,392 to Bardy et al discloses an automatic fibrillator for inclusion in an implantable defibrillator. Fibrillation is induced using overdrive pacing. The effective refractory period of the patient's heart is measured during pacing. A fibrillation inducing pulse is delivered at a calculated time interval following an overdrive pacing pulse. This approach requires complex timing calculations and may not be effective in all cases in inducing fibrillation.

U.S. Pat. No. 5,215,083 to Drane et al discloses an apparatus and method for fibrillation induction. At least a portion of a pulse train of "micro-shocks" delivered from the high voltage capacitors are synchronized to the patient's T-waves. The length of the series of trains and the microshock pulse widths are programmable parameters and the polarity of the shocks may be alternated within a train. This technique is also complex and may not be consistently effective.

Certain currently available ICDs have the capability for noninvasive induction and termination of arrhythmias to monitor and test the effectiveness of selected detection criteria and therapies. For example, the Ventak® Mini™ ICD available from Cardiac Pacemakers, Inc. may be slaved to an external laboratory stimulator to be used as a timing-signal source to allow signals communicated to the ICD via telemetry to be delivered to the patient with the same timing as the laboratory stimulator output. It also allows the ICD to deliver high-rate pulses through the defibrillation electrodes.

Another such commercially available ICD is the Jewel® ICD available from Medtronic, Inc. The Jewel ICD when used in connection with an external programmer provides certain electrophysiologic testing capabilities including the ability to confirm the inducibility of the patient's clinical arrhythmia and evaluation of the effectiveness of various ICD therapies in termination of the clinical arrhythmia. While this provides certain desirable testing features, it still lacks the full flexibility to allow the ICD to provide all of the functions of an external high voltage stimulator.

One problem with presently available system is that they provide only limited control over the implanted pulse generator timing and operation. Such control is needed to provide the capability and flexibility for full electrophysiologic testing deskable at the time of implant.

It is therefore an object of the invention to provide an ICD system which will provide improved flexibility for device based electrophysiologic testing.

It is another object of the invention to provide an ICD system which eliminates the need for an external defibrillator during implant procedures.

It is a further object of the invention to provide an ICD system which will allow a physician to control the timing of defibrillation shock delivery for a programmer commanded shock.

SUMMARY OF THE INVENTION

The present invention provides an improved ICD system and method for using such system for performing electrophysiologic (EP) testing of a patient using an ICD. The system includes an external programmer, implanted ICD and, in some embodiments, an external rescue shock generator. The system is used both at the time of implant and with follow-up testing. The external programmer communicates with the ICD through a telemetry link. At the time of implant, EP testing includes determining defibrillation thresholds of the patient. The physician has control over the timing of defibrillation shock delivery by the ICD during DFT and other EP testing. The high voltage (HV) capacitors are precharged to a desired voltage before arrhythmia is induced in the patient. Arrhythmia induction can be achieved, for example, by burst pacing or delivering current directly from the DC-to-DC converter to the patient's heart. Following charging of the HV capacitors, their voltage is periodically checked and if it falls below a prescribed level the capacitors are topped off. Once an arrhythmia is induced, a defibrillation shock may be delivered manually by the physician through the programmer or automatically based on the arrhythmia detection algorithms of the ICD. The delivery may be programmed to occur a prescribed time after arrhythmia induction or after arrhythmia detection. Whatever the prescribed trigger, the trigger directly delivers the shock rather than triggering HV capacitor charging. Shocks are preferably delivered synchronously at the next sensed event of pace time-out, but could be delivered asynchronously.

In a preferred embodiment of the invention, the system includes an external backup pulse generator for delivering a rescue shock through the ICD header and leads eliminating the need for an external defibrillator if the ICD therapy is unsuccessful and a rescue shock is required. The back-up pulse generator is connected to the lead system via a clip cable that is attached to the ICD via the setscrews in the ICD header.

The system of the invention provides advantages over using a separate piece of external test/stimulation equipment in that it is simpler to use and allows for a faster implant procedure. Further, there is no need to retest the DFT which is determined after implanting the ICD and, in the event the ICD housing is used as a defibrillation electrode, there is no need to provide a "test can" electrode for DFT testing.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

The present invention is directed to an implantable cardioverter-defibrillator (ICD) system having improved electrophysiologic (EP) testing capability. The system will first be described with reference to FIG. 1 and then the method of using the system for EP testing will be discussed with reference to FIG. 2.

Figure 1:
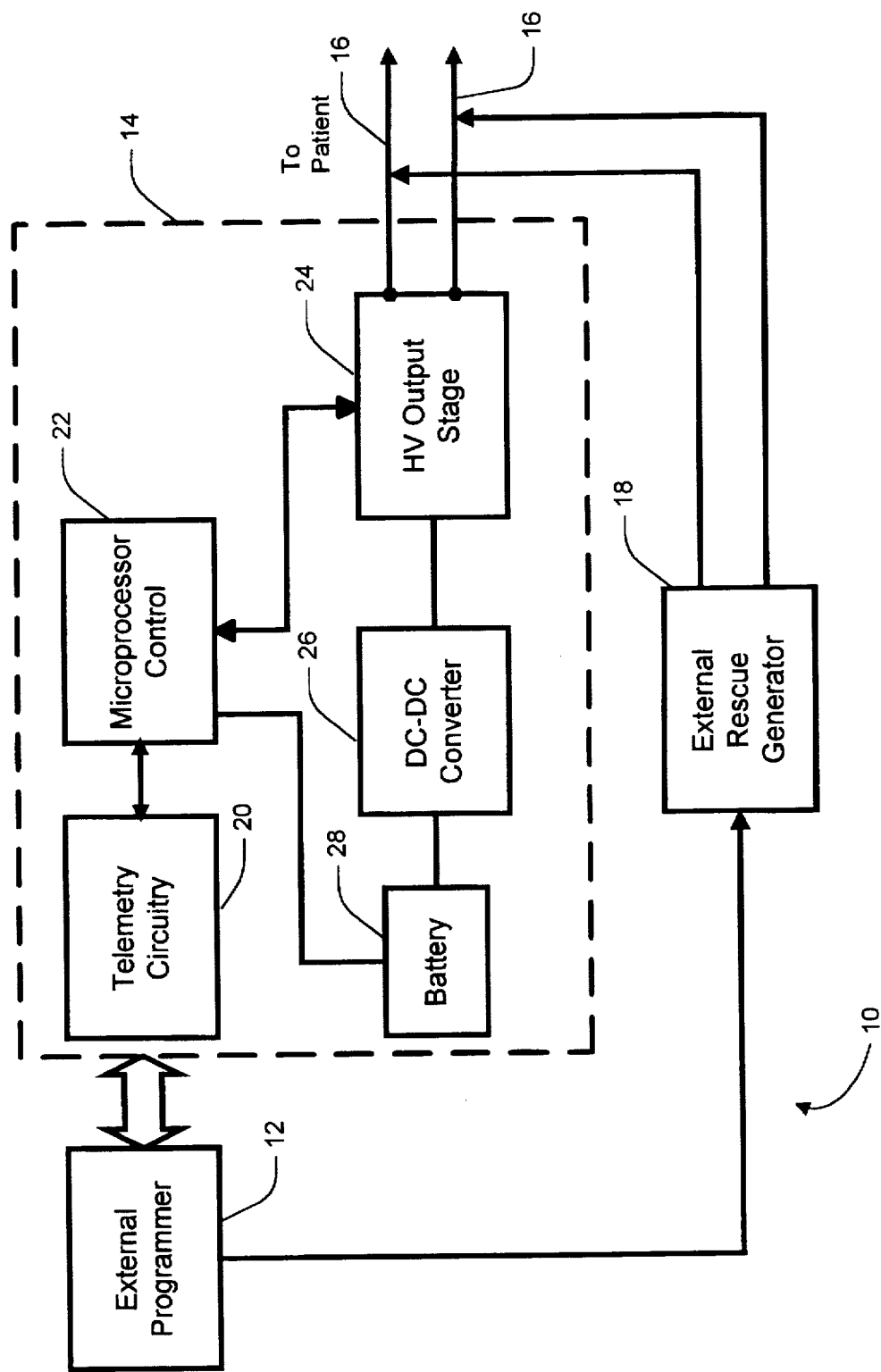
FIG. 1 is a simplified block diagram of the system of the invention.

FIG. 1 shows an ICD system 10 including an external programmer 12, an implantable pulse generator 14, an electrode system 16 and an external rescue generator 18. The external programmer 12 is typically a custom portable or laptop computer having a telemetry wand for communication with pulse generator 14 as is well known in the art. The external programmer 12 is capable of delivering commands to pulse generator 14 including interrogation of currently programmed diagnostic and therapy parameters and the ability to modify those parameters. It is also capable of downloading stored information from pulse generator 14 including stored electrograms as well as patient and device diagnostic data.

Pulse generator 14 includes a telemetry circuit 20 which enables communication between a microprocessor control circuit 22 and external programmer 12. There are many well know communication protocols which can be used in connection with the implementation of the present invention. The general operation of pulse generator 14 is controlled by microprocessor control circuit 22. It typically performs or supervises detection algorithms which monitor sensed electrograms from the patients heart to determine the presence or absence of an arrhythmia. Electrogram signals are received from various electrodes placed in or near the patient's heart as is well known in the art. If an arrhythmia is identified, appropriate pacing or high voltage therapy is delivered. The pacing circuitry is omitted for simplicity.

High voltage therapy including cardioversion and defibrillation is delivered from high voltage output stage 24. The output stage 24 includes switching circuitry, preferably of the H-bridge type to allow delivery of biphasic waveforms. The output stage also includes the high voltage capacitors for storage and delivery of the cardioversion and defibrillation shocks. This could be a single capacitor or a bank of capacitors. The current preferred embodiment is two series connected aluminum electrolytic capacitors which together can be charged to about 750 volts and have a capacitance of about 100 to 150 microfarads. These numbers should not be taken as limiting since the present invention can be used in connection with the delivery of any high voltage defibrillation pulses. The capacitors are charged from a battery 28 by a DC-to-DC converter 26 under control of microprocessor 22. The high voltage pulses are delivered to the patient's heart through an electrode system 16. This may comprise any conventional electrode system including two or more defibrillation electrodes. For example, it may include one electrode on a transvenous lead in the right ventricle and a second electrode in the superior vena cava. The second electrode can be replaced or augmented by using the housing of pulse generator 14 as an electrode. Other electrodes such as epicardial patch electrodes are well known in the art.

External rescue generator 18 may be used with the system to provide a rescue shock in the event defibrillation shocks from implantable pulse generator 14 are ineffective in terminating an induced fibrillation. In a preferred embodiment of the invention it is slaved to external programmer 12 but it can also be operated manually. Connection to the external programmer is preferred both for simplicity of control and to provide an electrogram signal source to allow synchronous delivery of the rescue shocks. External rescue generator 18 is preferably capable of delivering a shock of up to about 50 joules directly through electrode system 16, avoiding the need for an external defibrillator. It is connected through a clip cable which is attached to pulse generator 14 via setscrews in the pulse generator header. In one header design known in the art, rubber septums cover the heads of setscrews in the device header. The setscrews are used to electrically and mechanically connect defibrillation lead connector pins to the pulse generator and are thus in direct electrical contact with the defibrillation electrodes. The septums hold pins of the clip cable in place against the setscrews during EP testing at the time of implantable pulse generator implant. If the pulse generator housing is used as an electrode, one connection to the external rescue generator 18 can be made by a direct connection to the housing.

As mentioned above, at the time an implantable cardioverter-defibrillator is implanted in a patient, the implanting physician performs EP testing to determine the optimum parameters for arrhythmia detection and therapy for the particular patient. Probably the most important part of this is setting the voltage or energy parameters for defibrillation therapy. The first step in this process is typically to determine the defibrillation threshold (DFT) for the patient. While there is no fixed energy threshold above which all defibrillation shocks are successful and below which all defibrillation shocks fall, an approximate energy level is determined which is a measure of the energy at which about half the shocks are successful and about half are unsuccessful. This is used as a baseline to which some desired safety margin is added. A typical safety margin may be about 10 joules. Thus if a DFT of 15 joules were determined, the ICD would be programmed to deliver a first defibrillation shock of 25 joules. It may also be determined from the DFT that the selected electrode configuration needs to be modified to reduce the patient's DFT or that a device with a higher (or lower) energy output should to be used. The method of the invention allows greater control and flexibility in performing this type of EP testing.

Figure 2:
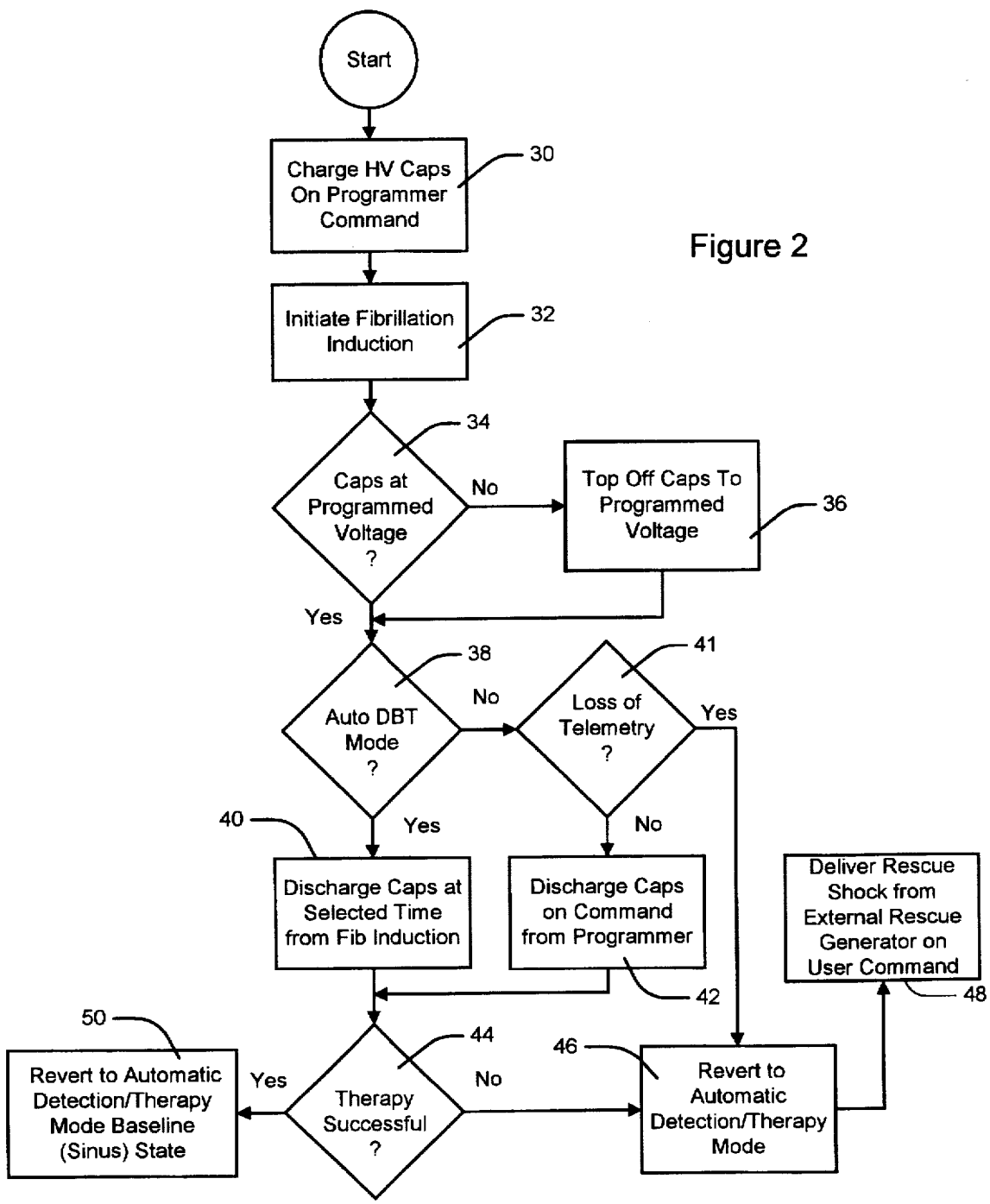
FIG. 2 is a flow chart illustrating the method of the invention.

Referring now to FIGS. 1 and 2, the method of the invention will now be discussed. At the time of an implant procedure, the physician will implant the implantable electrode system 16, typically one or more transvenous defibrillation leads and the pulse generator housing placed in a pocket formed in the patient's pectoral region. The leads are connected to the header of implantable pulse generator 14, typically by inserting the proximal lead connector pins in the header ports and tightening connector block setscrews. If external rescue generator 18 is being used, the clip cable is connected between external rescue generator 18 and the header. External rescue generator 18 is also connected to external programmer 12.

At this point the physician can initiate the DFT testing portion of the EP testing. The high voltage capacitors are precharged at step 30 to a programmed voltage (or energy). It will be understood that since the capacitance is fixed, the energy stored in the capacitor is directly related to the voltage to which the capacitor is charged determined by the formula:

$$E = \tfrac{1}{2}CV^2.$$

This precharging of the capacitors may be performed as a separate step initiated by the user or automatically as a part of the user's request to initiate a fibrillation induction sequence. After the capacitors are charged, a fibrillation induction sequence is initiated at step 32. Fibrillation induction may be achieved in any known manner such as delivery of a burst of pacing pulses or by directly coupling the output of the DC-to-DC converter to the heart. Periodically after the capacitors are precharged, their voltage is checked as illustrated at step 34 to determine if they need to be topped off. This step can be repeated until the capacitors are discharged to defibrillate the patient's heart. A voltage less than some preset amount below the selected voltage level, for example 10 volts, will trigger the topping off step 36. If the system is in an automatic device based testing (DBT) mode as determined at step 38, the capacitors are discharged at step 40 through the electrode system at a predetermined time following initiation of the induction sequence (or alternatively, timed from the end of the induction sequence.) The selected delay time may, for example, be a time between 1 and 20 seconds. If the system is in a manual DBT mode, a determination is made at step 41 of whether there has been a loss of telemetry as could be caused for example by removing the telemetry wand from proximity with the implantable pulse generator. If there has been no loss of telemetry, shock delivery may be manually triggered at step 42 from the programmer at the user's request. It should be noted that in prior art EP testing systems, the trigger initiates capacitor charging rather than shock delivery. Shocks are preferably delivered synchronously at the next sensed event or pace time-out, but could be delivered asynchronously.

In the manual DBT mode, a continued telemetry link between the pulse generator 14 and external programmer 12 is required to remain actively in this DBT mode. If the telemetry connection is lost in the manual DBT mode, pulse generator 14 will revert to its automatic detection/therapy operating mode as shown in step 46. Thus, the user may cancel the manual DBT mode at any time by removing the telemetry wand from its required close communication distance; alternatively, a cancel command may be sent from the external programmer. In the automatic DBT mode, the pulse generator 14 will deliver a shock when the selected delay time has elapsed regardless of whether or not the telemetry link is broken. The user may cancel a shock in the automatic DBT mode at any time between the end of the induction sequence and the shock delivery by sending a command from the external programmer.

After delivery of the shock, a determination is made at step 44 of whether or not the shock was successful in defibrillating the heart. If the shock was successful, the implantable pulse generator 14 reverts back to its automatic detection/therapy mode baseline state for a sinus condition at step 50 and any additional needed DFT testing can be conducted by reinitiating the testing procedure. If the shock was unsuccessful in defibrillating the heart, the implantable pulse generator 14 reverts back to its automatic detection/therapy operating mode at step 44 using all currently programmed device parameters. In a preferred embodiment of the invention, the unsuccessful shock is treated as the first in the programmed therapy sequence. This includes using fibrillation redetection parameters following an unsuccessful shock instead of initial detection parameters and delivering the second shock programmed in the sequence.

If it is determined that the implantable pulse generator will not be effective and a rescue shock is necessary, rescue pulse generator 18 is commanded at step 48 to deliver a rescue shock (either at a preprogrammed level or a fixed maximum output, e.g., 50 joules) through the electrode system 16.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable pulse generator system having electrophysiologic testing capability, said system comprising:

an external programmer for providing control commands;

an implantable pulse generator including telemetry circuitry for communication with said external programmer, a microprocessor coupled to said telemetry circuitry for controlling the operation of said pulse generator, a fibrillation induction circuit, capacitor means for storing electrical energy, a battery, and a charging system for charging said capacitor means from said battery, said fibrillation induction circuit deriving energy for delivery of an electrical signal from a source other than said capacitor means;

an electrode system for discharging stored energy in said capacitor means into said patient's heart; and said microprocessor being programmed for an electrophysiologic testing mode to charge said capacitor means to a voltage level for defibrillation upon command from said external programmer and prior to activation of said fibrillation induction circuit, to induce fibrillation with said fibrillation induction circuit and to discharge said capacitor means upon either command from said external programmer or at a prescribed time following induction of fibrillation by said fibrillation induction circuit.

2. The system of claim 1 and further including an external rescue generator for delivering a rescue shock to said patient's heart, said external rescue generator coupled to said electrode system through said implantable pulse generator.

3. The system of claim 1 wherein said microprocessor of said implantable pulse generator is further programmed to default to an automatic detection/therapy operating mode if a first discharge of said capacitor means fails to terminate an induced fibrillation condition.

4. The system of claim 1 wherein said microprocessor of said implantable pulse generator is further programmed to default to an automatic detection/therapy operating mode if telemetry between said implantable pulse generator and said external programmer is interrupted.

5. A method for performing electrophysiologic testing on a patient's heart using an implantable pulse generator system, said system comprising an implantable pulse generator having a capacitor means for storing electrical energy to defibrillate said patient's heart, an electrode system for discharging said stored energy into said patient's heart, and an external programmer for communication with and command of said implantable pulse generator, said method comprising the steps of:

charging said capacitor means to a selected energy level upon command and from said external programmer to said implantable pulse generator;

inducing a fibrillation rhythm in said patient's heart following said charging step; and discharging said stored energy of said selected energy level through said electrode system into said patient's heart to defibrillate said patient's heart.

6. The method of claim 5 and further including the step of said implantable pulse generator detecting said fibrillation rhythm.

7. The method of claim 5 wherein said step of defibrillating includes delaying a selected time following initiating said inducing step before discharging said stored energy.

8. The method of claim 5 wherein said step of defibrillating includes said implantable pulse generator monitoring an electrical signal from said patient's heart and discharging said stored energy synchronous with a sensed cardiac event.

9. The method of claim 5 wherein said step of defibrillating includes delaying a selected time following concluding said inducing step before discharging said capacitor means.

10. The method of claim 5 and further including the step following said charging step of periodically monitoring the energy level of said capacitor means and charging said capacitor means back to said selected level if said energy level falls to less than a prescribed amount below said selected level.

11. The method of claim 5 wherein said pulse generator reverts to an automatic detection/therapy operating mode if said discharging step fails to defibrillate said patient's heart.

12. The method of claim 5 wherein a rescue shock is delivered through said electrode system from an external defibrillator if said discharging step fails to defibrillate said patient's heart.

13. The method of claim 5 wherein said steps of charging said storage element upon command from said external programmer and inducing a fibrillation rhythm are both performed in response to a single command from said external programmer.

14. The method of claim 5 wherein said step of discharging said stored energy is performed in response to a separate manual command to said external programmer from a user.

15. The method of claim 5 and further including the steps of:

establishing a telemetry link between said implantable pulse generator and said external programmer; and in the event of a loss of said telemetry link between said implantable pulse generator and said external programmer reverting said implantable pulse generator to an automatic detection/therapy mode.

* * * * *